(12) United States Patent
Yerxa et al.

(10) Patent No.: US 6,436,910 B1
(45) Date of Patent: *Aug. 20, 2002

(54) METHOD OF PROMOTING MUCOSAL HYDRATION WITH CERTAIN URIDINE, ADENINE AND CYTIDINE DIPHOSPHATES AND ANALOGS THEREOF

(75) Inventors: Benjamin R. Yerxa; Janet L. Rideout, both of Raleigh; Arthur C. Jones, Durham, all of NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/005,267

(22) Filed: Dec. 3, 2001

Related U.S. Application Data

(63) Continuation of application No. 09/512,867, filed on Feb. 25, 2000, now Pat. No. 6,331,529.
(60) Provisional application No. 60/121,754, filed on Feb. 26, 1999.

(51) Int. Cl.$^7$ ............................................... A61K 31/70
(52) U.S. Cl. ............................ 514/47; 514/51; 514/912
(58) Field of Search ........................... 514/47, 51, 912

(56) References Cited

U.S. PATENT DOCUMENTS

| | | | | |
|---|---|---|---|---|
| 4,753,945 | A | 6/1988 | Gilbard et al. | 514/263 |
| 4,868,154 | A | 9/1989 | Gilbard et al. | 514/13 |
| 5,789,391 | A | 8/1998 | Jacobus et al. | 514/51 |

FOREIGN PATENT DOCUMENTS

| | | |
|---|---|---|
| WO | WO 96 40059 | 12/1996 |
| WO | WO 97 05195 | 2/1997 |
| WO | WO 98 03177 | 1/1998 |
| WO | WO 98/34942 | 8/1998 |
| WO | PCT/US00/05282 | 2/2000 |

OTHER PUBLICATIONS

Lazarowski, et al., UDP activates a mucosal–restricted receptor on human nasal epithelial cels that is distinct from the P2Y2 receptor:, *Proceedings of the National Academy of Sciences of the USA*, 94(6):2599–2603 (1997).
Mason, et al., "Regulation of transepithelial ion transport and intracellular calcium by extracellular ATP in human normal and systic fibrosis airway epithelium", *British Journal of Pharmacology*, 103(3):1649–1656 (1991).
Bhadauria, et al., Genital tract abnormalities and female sexual function impairment in systemic sclerosis, *Am. J. Obstet. Gynecol.*, 172:580–587 (1995).
Cust, et al., "Consequence and treatment of ovarian failure after total body irradiation for leukaemia," *Br. Med. J.*, 299:1494–1497 (1989).
Fowler, et al., "Effect of $CO_2$ Laser Conization of the Cervix on Pathologic Interpretation of the Cervical Intraepithelial Neoplasia," *Obstet. Gynecol.*, 79(5):693–698 (1992).
Gilbard, et al., "Treatment of Keratoconjunctivitis Sicca in Rabbits with 3–Isobutyl–1–Methylxanthine," *Arch. Ophthal.*, 112:1614–1616 (1994).
Gilbard, et al., "Stimulation of Tear Secretion and Treatment of Dry–Eye Disease with 3–Isobutyl–1–methylxanthine," *Arch. Ophthal.*, 109:672–676 (1991).
Gray, et al., "Mucociliary Differentation of Serially Passaged Normal Human Tracheobronchial Epithelia Cells," *Am. J. Respir. Cell Mol. Biol.*, 14:104–112 (1996).
Key, "Management of Vaginal Dryness," *Nurs. Stand.*, 5:24–27 (1991).
Lemp, "Is the Dry Eye Contact Lens Wearer at Risk? Yes," *Cornea*, 9(1):S48–S50 (1990).
Marchesoni, et al., "Gynaecological aspects of primary Sjogren's syndrome," *Eur. J. Obstet. Gynecol. Reprod. Biol.*, 63:49–53 (1995).
Moss and Parsons, "Current Estimates From the National Health Interview Survey," DHHS Publication No. (PHS) 86–1558, pp. 66–67 (1986).
Ng et al., "The action of a water–soluble carbodiimide on adenosine–5'–polyphosphates," *Nucleic Acids Res.*, 15(8):3572–3580 (1987).
Rapaport, et al., "HeLa cell DNA polymerase α is tightly associated with tryptophanyl–tRNA synthetase and diadenosine $5',5''-P^1$, $P^4$–tetraphosphate binding activities," *Proc. Natl. Acad. Sci. USA*, 89:838–842 (1981).
Reginald, et al., "Medroxyprogesterone acetate in the treatment of pelvic pain due to venous congestion," *Br.J. Obstet. Gynaecol.*, 96:1148–1152 (1989).
Rolando, et al., "Ocular Surface Changes Induced by Repeated Impression Cytology," *Adv. Exp. Med. Bio.*, 350:249–254 (1994).

(List continued on next page.)

*Primary Examiner*—Zohreh Fay
(74) *Attorney, Agent, or Firm*—Alberta P. Halluin; Viola T. Kung; Howrey Simon Arnold & White, LLP

(57) ABSTRACT

A method and preparation for the stimulation of mucosal hydration in a subject in need of such treatment is disclosed. The method comprises administering to the mucosal surfaces of the subject a purinergic receptor agonist such as uridine 5'-diphosphate (UDP), dinucleotide triphosphates; cytidine 5'-diphosphate (CDP), adenosine 5'-diphosphate (ADP), or their therapeutically useful analogs and derivatives, in an amount effective to stimulate mucin secretion. Pharmaceutical formulations and methods of making the same are also disclosed. Methods of administering the same would include: topical administration via a liquid, gel, cream, or as part of a contact lens or selective release membrane; or systemic administration via nasal drops or spray, inhalation by nebulizer or other device, oral form (liquid or pill), injectable, intra-operative instillation or suppository form. A method for facilitating the expectoration of sputum for the purpose of detecting cellular abnormalities indicative of lung disease is also disclosed.

12 Claims, 1 Drawing Sheet

OTHER PUBLICATIONS

Sorokin, et al., "Obstetric and Gynecologic Dysfunction in the Ehlers–Danlos Syndrome," *J. Reprod. Med.,* 39:281–284 (1994).

Sreebny, et al., "Xerostomia in Diabetes Mellitus," *Diabetes Care,* 15(7):900–904 (1992).

Stumpf, "Pharmacokinetics of Estrogen," *Obstet, Gynecol.,* 75(4):9S–14S (1990).

Whitehead, et al., "Effects of Estrogen and Progestins on the Biochemistry and Morphology of the Postmenopausal Endometrium," *N. Eng. J. Med.,* 305:1599–1605 (1981).

Wisniewski, et al., "Postpartum vaginal atrophy," *Am. J. Obstet. Gynecol.,* 165:1249–1254 (1991).

METHOD OF PROMOTING MUCOSAL HYDRATION WITH CERTAIN URIDINE, ADENINE AND CYTIDINE DIPHOSPHATES AND ANALOGS THEREOF

This application is a continuation of U.S. application Ser. No. 09/512,867, filed Feb. 25, 2000 now U.S. Pat. No. 6,331,529; which claims the benefit of U.S. Provisional Application No. 60/121,754, filed Feb. 26, 1999.

TECHNICAL FIELD

This invention relates to a method of regulating secretions in and around the mucous membranes of a mammal by administering purinergic receptor agonists such as certain uridine, adenine, or cytidine diphosphates as well as other nucleoside phosphate compounds.

BACKGROUND OF THE INVENTION

There are many situations where it is therapeutically desirable to increase the amount of hydration on mucosal surfaces of the body. Mucus membranes are hydrated surface epithelial tissues that line cavities exposed to the outside environment. These mucosal surfaces of the body must stay hydrated with the proper mixtures of water, salt, mucin and other proteins in order to defend the body from the outside world and remain comfortable. The mucus membranes play a major role in fighting off infections and keeping the exposed organs clean and healthy. Mucus membranes are found on the surface of the eye, vagina, sinonasal cavities and mouth (oropharyngeal). Impaired hydration of these mucus membranes leads to medical conditions such as: dry eye, vaginal dryness, rhinosinusitis, dry mouth, corneal injury, and others.

Dry eye disease is the general term for indications in which the mucous membranes surrounding the eye are not properly hydrated due to an imbalance of salt, water and mucus in the precorneal tear film. Dry eye is characterized by a decrease in tear production or an increase in tear film evaporation, together with the ocular surface disease that results. Approximately 38 million Americans are affected with some type of dry eye disorder. Among the indications that are referred to by the general term "dry eye disease" are: keratoconjunctivitis sicca (KCS), age-related dry eye, Stevens-Johnson syndrome, Sjogren's syndrome, ocular cicatrical pemphigoid, blepharitis, corneal injury, infection, Riley-Day syndrome, congenital alacrima, nutritional disorders or deficiencies (including vitamin deficiencies), pharmacologic side effects, eye stress and glandular and tissue destruction, environmental exposure to smog, smoke, excessively dry air, airborne particulates, autoimmune and other immunodeficient disorders, and comatose patients rendered unable to blink. The present invention may also be useful as a wash or irrigation solution in conscious individuals, during surgery or to maintain comatose patients or those who cannot blink due to neuromuscular blockade or loss of the eyelids.

Currently, the pharmaceutical treatment of dry eye disease is mostly limited to administration of artificial tears (saline solution) to temporarily rehydrate the eyes. However, relief is short-lived and frequent dosing is necessary. In addition, artificial tears often have contra-indications and incompatibility with soft contact lenses (M. Lemp, Cornea 9(1): S48–550 (1990)). The use of phosphodiesterase inhibitors, such as 3-isobutyl-1-methylxanthine (IBMX) to stimulate tear secretion is disclosed in U.S. Pat. No. 4,753,945. The effectiveness of these phosphodiesterase inhibitors is currently being investigated (J. Gilbard, et al., Arch. Ophthal. 112:1614–16 (1994) and 109:672–76 (1991); idem, Inv. Ophthal. Vis. Sci. 31:1381–88 (1990) Stimulation of tear secretion by topical application of melanocyte stimulating hormones is described in U.S. Pat. No. 4,868,154.

Vaginal dryness is a very common problem which brings physical and emotional distress to many women (E. Key, Nurs. Stand. 5:24–27 (1991)). It most commonly manifests itself during sexual intercourse, which causes dyspareunia and can eventually lead to apareunia. Although it is traditionally considered to be a condition which affects post-menopausal women, it can occur during the premenopausal and perimenopausal years. The use of oral contraceptives may also cause a reduction in vaginal moisture in some women (W. Reginald, et al., Br. J. Obstet. Gynaecol. 96:1148–1152 (1989)). Postpartum vaginal dryness, independent of or as a result of lactation, can be a significant complaint (P. Wisniewski, et al., Am. J. Obstet. Gynecol. 165:1249–1254 (1991)). Women undergoing chemotherapy or radiotherapy for malignant diseases such as leukemia often experience vaginal dryness as a result of treatment (M. Cust, et al., Br. Med. J. 299:1494–1497 (1989)). Many disease states, such as systemic sclerosis and other systemic autoimmune disorders (S. Bhadauria, et al., Am. J. Obstet. Gynecol. 172:580–587 (1995)), Ehlers-Danlos syndrome (Y. Sorokin, et al., J. Reprod Med. 39:281–284 (1994)), diabetes mellitus (L. Sreebny, et al., Diabetes Care 15:900–904 (1992)), and Sjögren's syndrome (D. Marchesoni, et al., Eur. J. Obstet. Gynecol. Reprod. Biol. 63:49–53 (1995)) have decreased vaginal hydration and lubrication problems as significant disease-associated symptoms.

Current therapies for increasing vaginal moisture are: lubricating agents such as lubricating creams or jellies, topical estrogen creams, and HRT (hormone replacement therapy). Lubricating jellies provide short-lived and temporary relief, as these are aqueous preparations containing no pharmacologically active agent. Topical estrogen creams, if used on a regular basis, may be absorbed into the systemic circulation. This can cause endometrial stimulation and can lead to endometrial hyperplasia and carcinoma (M. Whitehead, et al., N. Eng. J. Med. 305:1599–1605 (1981)). HRT is effective at relieving symptoms of vaginal atrophy and hence vaginal dryness but has several contraindications and unwanted risks and side effects.

Another disease state characterized by improper hydration of mucus secretions is acute and chronic sinusitis, or rhinosinusitis as it is currently referred to by otolaryngologists. Rhinosinusitis is a disease of the paranasal sinuses typically associated with retained, thick mucus secretions. It is this country's most common health-care complaint, affecting an estimated 31 million people (A. Moss and V. Parsons, National Center for Health Statistics, 1986: 66–7, DHHS Publication No. (PHS) 86–1588 (1985)).

Dry mouth is a condition in which the mucus membranes of the oropharyngeal cavity becomes dehydrated, leading to discomfort, difficulty swallowing and bad breath. Among the conditions generally referred to as "dry mouth" are, but not limited to: Sjogren's syndrome, chemotherapy and post radiation treatment, and pharmacologic side effects.

Thus, as a result of the ineffectiveness and risks of current therapies, medical researchers have sought to develop alternatives for the treatment of dehydrated mucus membranes. Use of UDP and ADP for the purpose of treating pulmonary disorders characterized by the retention of lung mucus secretions is described in Patent Application (Boucher, R. C., Jr., et al., PCT/US98/17894). Applicants were motivated to investigate whether UDP and other P2Y$_6$ receptor agonists could stimulate hydration and mucin production on mucosal surfaces throughout the body, such as in the eye, female reproductive tract, sinonasal and oropharyngeal cavities.

Applicant has discovered that ion, mucin and fluid secretion can be stimulated from mucous membrane tissues via P2Y$_6$ purinergic receptor-mediated mechanisms. UDP and other purinergic receptor agonists, administered topically or systemically, provide a novel method of treating disorders of mucosal hydration.

Applicant has also discovered that UDP and other diphosphate agonists of the P2Y$_6$ receptor also facilitate expectoration of deep lung mucus. Such expectoration is useful in a method of diagnosing lung diseases whereby the expectorated deep lung mucus is analyzed for cytological abnormalities indicative of lung disease, such as lung cancer and tubeculosis.

SUMMARY OF THE INVENTION

A method of stimulating mucosal hydration in a subject in need of such treatment is disclosed. The method of the present invention may be used to increase mucosal hydration for any reason, including, but not limited to, treatment of dry eye disease, vaginal dryness, rhinosinusitis and dry mouth.

Dry eye disease is defined to include: keratoconjunctivitis sicca (KCS), age-related dry eye, Stevens-Johnson syndrome, Sjogren's syndrome, ocular cicatrical pemphigoid, blepharitis, corneal injury, infection, Riley-Day syndrome, congenital alacrima, nutritional disorders or deficiencies (including vitamin), pharmacologic side effects, eye stress and glandular and tissue destruction, environmental exposure to smog, smoke, excessively dry air, airborne particulates, autoimmune and other immunodeficient disorders, and comatose patients rendered unable to blink. The present invention may also be useful as an ophthalmic wash or irrigation solution in conscious individuals, during surgery (e.g. lasik, radial keratotomy, cataract removal) or to maintain comatose patients or those who cannot blink due to neuromuscular blockade, muscle or nerve damage, or loss of the eyelids. The compound uridine diphosphate (UDP) was found to be a potent stimulator of mucin secretion in tissue preparations containing goblet cells. Furthermore, an in vivo example of mucin secretion in accordance with the invention is conducted on an animal using impression cytology.

A method of stimulating cervical and vaginal secretions in a subject in need of such treatment is disclosed. The method of the present invention may be used to increase cervical and vaginal secretions for any reason, including, but not limited to, treatment of vaginal dryness. Vaginal dryness is associated with but not limited to menopause, childbirth, breastfeeding, chemotherapy or radiotherapy, diabetes mellitus, Sjogren's syndrome, Ehlers-Danlos syndrome, systemic sclerosis and other systemic autoimmune diseases, hysterectomy, urogenital surgery, psychosomatic disorders, anxiety, psychosexual problems, and pharmacological drug-related side effects.

Furthermore, because of their general ability to rehydrate mucosal surfaces, the compounds of the present invention may also be useful in the treatment of rhinosinusitis and dry mouth. Additionally, it is postulated that the compounds of the present invention could be useful for the treatment of dry mouth.

The method of the present invention comprises administering a P2Y$_6$ receptor agonist: uridine 5'-diphosphate, P$^1$,P$^3$-di(uridine-5')triphosphate, cytidine 5'-diphosphate or adenosine 5'-diphosphate or analogs thereof, in an amount effective to stimulate mucosal hydration.

Another aspect of the present invention is the use of uridine 5'-diphosphate, P$^1$, P$^3$-di(uridine-5')triphosphate, cytidine 5'-diphosphate or adenosine 5'-diphosphate or analogs thereof, for the manufacture of a medicament for carrying out a therapeutic method of treatment as given above.

The present invention also discloses pharmaceutical compositions comprising uridine 5'-diphosphate, P$^1$,P$^3$-di(uridine-5')triphosphate, cytidine 5'-diphosphate or adenosine 5'-diphosphate or analogs thereof, with a pharmaceutical carrier therefor.

The present invention also discloses a method of detecting lung disease comprising administering uridine 5'-diphosphate, P$^1$,P$^3$-di(uridine-5')triphosphate, cytidine 5'-diphosphate or adenosine 5'-diphosphate or analogs thereof, to at least one lung of an individual in order to facilitate the obtaining of a deep lung mucus, i.e., sputum sample, whereby the sputum sample is subjected to cytological, immunocytochemical, bacterial, or DNA analysis (e.g., via PCR) for detecting cellular abnormalities in the lung epithelium. The lung diseases detectable by this method include, but are not limited to lung cancer and tuberculosis. A preferred diphosphate compound for this diagnostic method is UDP (uridine 5'-diphosphate).

DETAILED DESCRIPTION OF THE INVENTION

Figure 1:
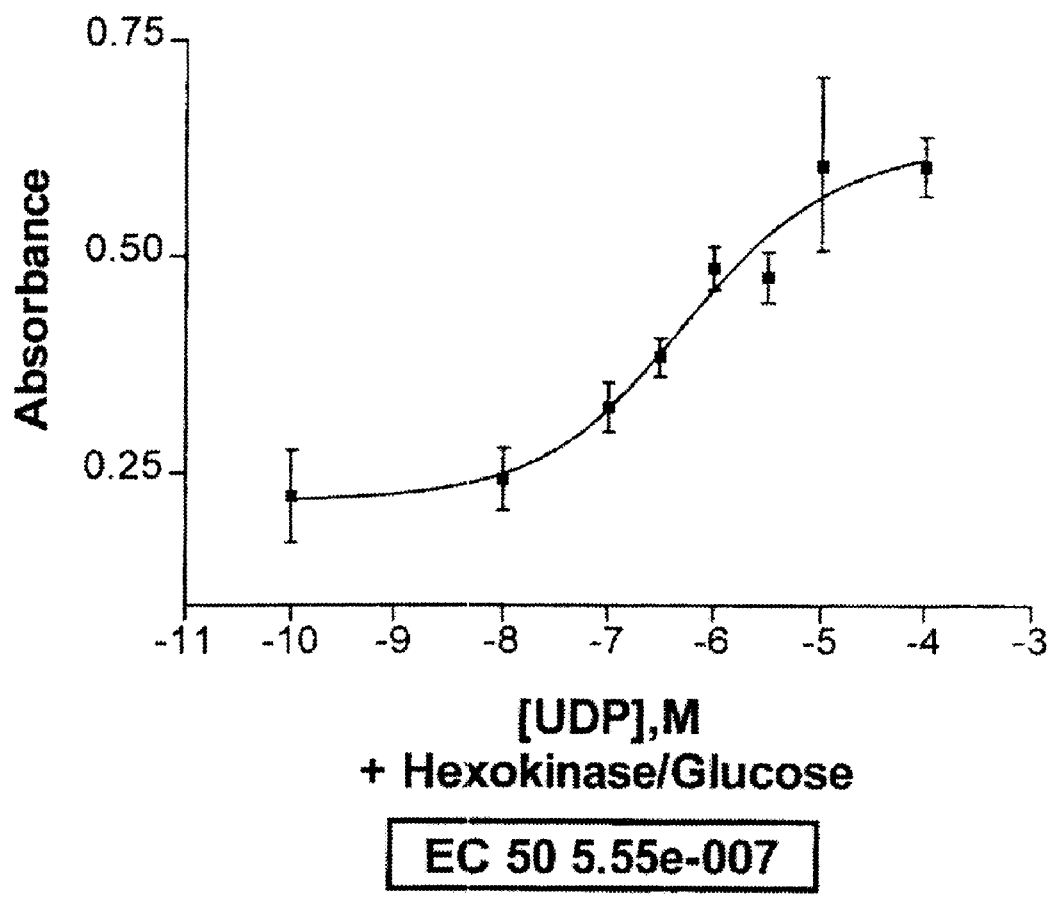
FIG. 1 shows mucin secretion in normal human bronchial/tracheal epithelia cells (Donor #8F0258) in response to different concentrations of UDP.

The method of the present invention may be used to increase mucosal hydration for any reason, including, but not limited to, treatment of dry eye disease, vaginal dryness, rhinosinusitis and dry mouth. Dry eye disease is defined to include: keratoconjunctivitis sicca (KCS), age-related dry eye, Stevens-Johnson syndrome, Sjogren's syndrome, ocular cicatrical pemphigoid, blepharitis, corneal injury, infection, Riley-Day syndrome, congenital alacrima, nutritional disorders or deficiencies (including vitamin), pharmacologic side effects, eye stress and glandular and tissue destruction, environmental exposure to smog, smoke, excessively dry air, airborne particulates, autoimmune and other immunodeficient disorders, and comatose patients rendered unable to blink. The present invention may also be useful as an ophthalmic wash or irrigation solution in conscious individuals, during surgery or to maintain comatose patients or those who cannot blink due to muscle or nerve damage, neuromuscular blockade or loss of the eyelids.

Applicants have discovered that uridine 5'-diphosphate (UDP) and related compounds are potent agonists for purinergic receptors found in cervical and vaginal mucus membrane preparations. The methods of the present invention are an improvement upon the current most commonly used treatments of vaginal dryness because UDP stimulates a patient's own production and secretion of mucins as well as increasing the levels of mucosal hydration, which serve to maintain the natural protective and lubricant characteristics of vaginal and cervical mucosa. The methods of the present invention may also be used exclusive of, or as an adjunct to, hormone replacement therapy (HRT) or estrogen replacement therapy (ERT).

Another disease state characterized by improper hydration of mucus secretions is sinusitis. Sinusitis is a disease of the paranasal sinuses typically associated with retained, thick mucus secretions.

Dry mouth is a condition in which the mucus membranes of the oropharyngeal cavity becomes dehydrated, leading to discomfort, difficulty swallowing and bad breath. Among the conditions generally referred to as "dry mouth" are, but not limited to: Sjogren's syndrome, chemotherapy and post radiation treatment, and pharmacologic side effects.

Applicant has discovered that uridine 5'-diphosphate (UDP) is a potent agonist for purinergic receptors found in mucus membrane preparations. The method of the present invention is an improvement upon the current most commonly used treatment of impaired mucosal hydration—artificial tears (i.e., saline solution) for dry eye; oily lubricants for vaginal drynesss; saline irrigation or decongestants for sinusitis; artificial saliva or Salagen for dry mouth. Because UDP stimulates a patient's own mucosal hydration mechanisms, it maintains the natural protective and lubricant characteristics. Furthermore, the method of the present invention may be useful even where mucosal glands are dysfunctional or absent.

The present invention also discloses a method of detecting lung disease comprising administering uridine 5'-diphosphate, $P^1,P^3$-di(uridine-5')triphosphate, cytidine 5'-diphosphate or adenosine 5'-diphosphate or analogs thereof, to at least one lung of an individual in order to facilitate the obtaining of a deep lung mucus, i.e., sputum sample, whereby the sputum sample is subjected to cytological, immunocytochemical, bacterial, or DNA analysis (e.g., via PCR) for detecting cellular abnormalities in the lung epithelium. The lung diseases detectable by this method include, but are not limited to lung cancer and tuberculosis. A preferred diphosphate compound for this diagnostic method is UDP (uridine 5'-diphosphate). Prior to analysis of the sputum sample, the sputum sample may first be digested with a liquefying agent, such as N-acetyl-L-cystein (NALC) and sodium hydroxide.

The present invention provides a method of stimulating mucosal hydration in a mammal, including a human, in need thereof comprising administering an amount of a compound of Formulas I, II, III, or IV or a pharmaceutically acceptable ester or salt thereof effective to increase said hydration.

UDP and its analogs are depicted in general Formula I:

Formula I wherein:
$X_1$ and $X_2$ are each independently either $O^-$ or $S^-$; preferably, $X_1$ and $X_2$ are $O^-$;
$R_1$ is O, imido, methylene or dihalomethylene (e.g., dichloromethylene or difluoromethylene); preferably, $R_1$ is oxygen or difluoromethylene;
$R_2$ is selected from the group consisting of H, halo, alkyl, substituted alkyl, optionally substituted alkenyl, optionally substituted alkynyl, alkoxyl, nitro and azido; preferably, $R_2$ is H; particularly preferred compounds of Formula I are uridine 5'-diphosphate (UDP) and uridine 5'-O-(2-thiodiphosphate) (UDPβS).

A dinucleotide is depicted by the general Formula II:

wherein:
X is oxygen, methylene, difluoromethylene, or imido;
B and B' are each independently a purine residue or a pyrimidine residue linked through the 9- or 1- position, respectively;
Z=OH or $N_3$;
Z'=OH or $N_3$;
Y=H or OH;
Y'=H or OH;
provided that when Z is $N_3$, Y is H or when Z' is $N_3$, Y' is H.

The furanose sugar is preferably in the β-configuration.
The furanose sugar is most preferably in the β-D-configuration.

Preferred compounds of Formula II are the compounds of Formula IIa:

Formula IIa wherein:
X=O;
Z, Z', Y, and Y'=OH;
B and B' are defined in Formulas IIc and IId;
Z, Z', Y, and Y'=OH;
B=uracil;
B' is defined in Formulas IIc and IId; or
X=O;
Z, Y, and Z'=OH;
$Y^1$=H;
B=uracil;
B' is defined in Formulas IIc and IId; or
X=O;
Z and Y=OH;
Z'=$N_3$;
Y'=H;
B=uracil;
B'=thymine; or
X=O;
Z and Z'=$N_3$;
Y and Y'=H;
B and B'=thymine; or
X=$CH_2$, $CF_2$, or NH;

Z, Z', Y, and Y'=OH;

B and B' are defined in Formulas IIc and IId.

Another preferred group of the compounds of Formula II are the compounds of Formula IIb or the pharmaceutically acceptable salts thereof:

Formula IIb

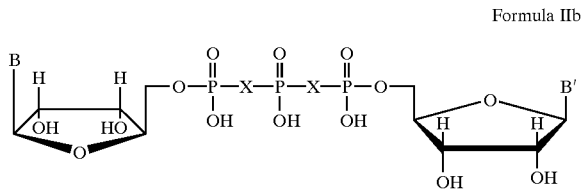

wherein:

X is oxygen, methylene, difluoromethylene, or imido; and

B and B' are each independently a purine residue, as in Formula IIc, or a pyrimidine residue, as in Formula IId, linked through the 9- or 1- position, respectively. In the instance where B and B' are uracil, attached at N-1 position to the ribosyl moiety, then the total of m+n may equal 3 or 4 when X is oxygen. The ribosyl moieties are in the D- configuration, as shown, but may be L-, or D- and L-. The D- configuration is preferred.

Formula IIc

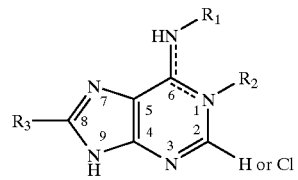

wherein $R_1$ is hydrogen, $C_{1-8}$alkyl, $C_{3-6}$ cycloalkyl, phenyl, or phenyloxy, wherein at least one hydrogen of said $C_{1-8}$alkyl, phenyl, phenyloxy, is optionally substituted with a moiety selected from the group consisting of halogen, hydroxy, $C_{1-4}$alkoxy, $C_{1-4}$alkyl, $C_{6-10}$aryl, carboxy, cyano, nitro, sulfonamido, sulfonate, phosphate, sulfonic acid, amino, $C_{1-4}$alkylamino, di-$C_{1-4}$ alkylamino wherein said alkyl groups are optionally linked to form a heterocycle, ω-A(alkyl)CONH(alkyl)-,and ω-A(alkyl)NHCO(alkyl)-, wherein A is amino, mercapto, hydroxy or carboxyl;

$R_2$ is O or is absent; or $R_1$ and $R_2$ taken together form a 5-membered ffised imidazole ring optionally substituted on the 4- or 5- positions of the etheno moiety with $C_{1-4}$alkyl, phenyl or phenyloxy, wherein at least one hydrogen of said $C_{1-4}$alkyl, phenyl, phenyloxy, is optionally substituted with a moiety selected from the group consisting of halogen, hydroxy, $C_{1-4}$alkoxy, $C_{1-4}$alkyl, $C_{6-10}$aryl, $C_{7-12}$arylalkyl, carboxy, cyano, nitro, sulfonamido, sulfonate, phosphate, sulfonic acid, amino, $C_{1-4}$ alkylamino, and di-$C_{1-4}$ alkylamino wherein said dialkyl groups are optionally linked to form a heterocycle; and $R_3$ is hydrogen, $NH_2$, $C_{1-8}$alkyl, $C_{3-6}$ cycloalkyl, phenyl; or phenyloxy, wherein at least one hydrogen of said $NH_2$, CC 4alkyl, phenyl, or phenyloxy, is optionally substituted with a moiety selected from the group consisting of halogen, hydroxy, $C_{1-4}$alkyl, $C_{6-10}$aryl, $C_{7-12}$arylalkyl, $C_{1-4}$alkoxy, $C_{7-12}$arylalkyloxy, $C_{1-4}$alkylthio, phenylthio, $C_{7-12}$arylalkylthio, carboxy, cyano, nitro, sulfonamido, sulfonate, phosphate, sulfonic acid, amino, $C_{1-4}$ alkylamino, phenylarnino, $C_{7-12}$arylalkyamino, di-$C_{1-4}$ alkyl amino wherein said dialkyl groups are optionally linked to form a heterocycle, ω-A(alkyl)CONH(alkyl)B—, and ω-A(alkyl)NHCO(alkyl)B—, wherein A and B are independently amino, mercapto, hydroxy or carboxyl.

The substituted derivatives of adenine (Formula IIc) include adenine 1-oxide; 1, N6-(4- or 5-substituted etheno) adenine; 6-substituted adenine; or 8-substituted aminoadenine, [6-aminohexyl]carbamoylmethyl-adenine; and ω-acylated- amino(hydroxy, thiol and carboxy)alkyl($C_{2-10}$)-adenine, wherein the acyl group is chosen from among, but not limited to, acetyl, trifluroroacetyl, benzoyl, substituted-benzoyl, etc., or the carboxylic moiety is present as its ester or amide derivative, for example, the ethyl or methyl ester or its methyl, ethyl or benzamido derivative.

Likewise, B or $B^1$ or both in Formula IIb may be a pyrimidine with the general formula of Figure IId, linked through the 1-position:

Formula IId

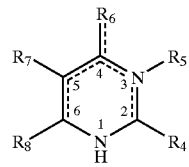

wherein:

$R_4$ is hydrogen, hydroxy, mercapto, amino, cyano, $C_{7-12}$arylalkoxy, $C_{1-6}$ alkylthio, $C_{1-6}$ alkoxy, $C_{-1-6}$ alkylamino or di$C_{1-4}$alkylamino, wherein the alkyl groups are optionally linked to form a heterocycle;

$R_5$ is hydrogen, acetyl, benzoyl, $C_{1-6}$ alkyl, phenyloxy, $C_{1-5}$ alkanoyl, aroyl, or sulphonate;

$R_6$ is hydroxy, mercapto, $C_{1-4}$alkoxy, $C_{7-12}$arylalkoxy, $C_{1-6}$alkylthio, amino, S-phenyl, $C_{1-5}$ disubstituted amino, triazolyl, $C_{1-6}$alkylarnino, or di-$C_{1-4}$alkylamino wherein said dialkyl groups are optionally linked to form a heterocycle or linked to $N^3$ to form a substituted ring; or $R_5$ and R6 taken together form a 5-membered fused imidazole ring between positions 3 and 4 of the pyrimidine ring and form a 3, $N^4$-ethenocytosine derivative, wherein said etheno moiety is optionally substituted on the 4- or 5- positions with $C_{1-4}$ alkyl; phenyl; or phenyloxy; wherein at least one hydrogen of said $C_{1-4}$alkyl; phenyl or phenyloxy is optionally substituted with a moiety selected from the group consisting of halogen, hydroxy, $C_{1-4}$alkoxy, $C_{1-4}$alkyl, $C_{6-10}$aryl, $C_{7-12}$arylalkyl, carboxy, cyano, nitro, sulfonamido, sulfonate, phosphate, sulfonic acid, amino, $C_{1-4}$ alkylamino, and di-$C_{1-4}$ alkylamino wherein said dialkyl groups are optionally linked to form a heterocycle;

$R_7$ is hydrogen, hydroxy, cyano, nitro, or $C_{2-8}$alkenyl; wherein said alkenyl moiety is optionally linked through an oxygen to form a ring, wherein at least one hydrogen of said alkenyl moiety on the carbon adjacent to said oxygen is optionally substituted with $C_{1-6}$alkyl, phenyl, substituted $C_{2-8}$alkynyl, halogen, substituted $C_{1-4}$alkyl, $CF_3$, $C_{2-3}$ alkenyl, $C_{2-3}$ alkynyl, allylamino bromovinyl, ethyl propenoate, or propenoic acid; or $R_6$ and $R_7$ together form a 5 or 6-membered saturated or unsaturated ring bonded through N or O at $R_6$, such ring optionally contains substituents that themselves contain functionalities; provided that when $R_8$ is amino or substituted amino, $R_7$ is hydrogen; and $R_8$ is hydrogen, amino or di-$C_{1-4}$alkylamino, $C_{1-4}$alkoxy, $C_{7-12}$arylalkoxy, $C_{1-4}$alkylthio, $C_{7-12}$arylalkylthio, carboxamidomethyl, carboxymethyl, methoxy, methylthio, phenoxy or phenylthio.

In the general structure of Figure IId above, the dotted lines in the 2- to 6-positions are intended to indicate the presence of single or double bonds in these positions; the relative positions of the double or single bonds being determined by whether the $R_4$, $R_6$, and $R_7$ substituents are capable of keto-enol tautomerism.

In the general structures of Figure IIc and IId above, the acyl groups advantageously comprise alkanoyl or aroyl groups. The alkyl groups advantageously contain 1 to 8 carbon atoms, particularly 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above mentioned alkenyl and alkynyl groups advantageously contain 2 to 8 carbon atoms, particulary 2 to 6 carbon atoms, e.g., ethenyl or ethynyl, optionally substituted by one or more appropriate substituents as described below. Appropriate substituents on the above-mentioned alkyl, alkenyl, alkynyl, and aryl groups are advantageously selected from halogen, hydroxy, $C_{1-4}$ alkoxy, $C_{1-4}$ alkyl, $C_{6-12}$ arylalkoxy, carboxy, cyano, nitro, sulfonamido, sulfonate, phosphate, sulfonic, amino, and substituted amino wherein the amino is singly or doubly substituted by a $C_{1-4}$ alkyl, and when doubly substituted, the alkyl groups optionally being linked to form a heterocycle.

CDP and its analogs are depicted by general Formula III:

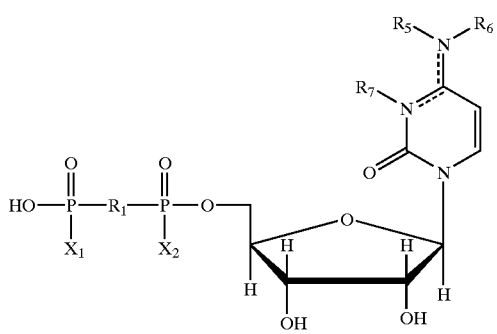

Formula III wherein:

$R_1$, $X_1$ and $X_2$ are defined as in Formula I;

$R_5$ and $R_6$ are H while $R_7$ is nothing and there is a double bond between N-3 and C-4 (cytosine), or $R_5$, $R_6$ and $R_7$ taken together are —CH=CH—, forming a ring from N-3 to N-4 with a double bond between N-4 and C-4 (3, $N^4$-ethenocytosine) optionally substituted at the 4- or 5-position of the etheno ring. ADP and its analogs are depicted by general Formula IV:

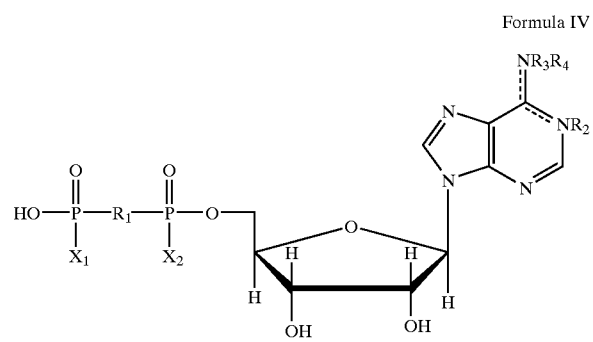

Formula IV wherein:

$R_1$, $X_1$ and $X_2$ are defined as in Formula I;

$R_3$ and $R_4$ are H while $R_2$ is nothing and there is a double bond between N-1 and C-6 (adenine), or $R_3$ and $R_4$ are H while $R_2$ is O and there is a double bond between N-1 and C-6 (adenine 1-oxide), or $R_3$, $R_4$, and $R_2$ taken together are —CH=CH—, forming a ring from N-6 to N-1 with a double bond between N-6 and C-6 (1,N6-ethenoadenine).

For simplicity, Formulas I, II, III, and IV herein illustrate the active compounds in the naturally occurring D-configuration, but the present invention also encompasses compounds in the L-configuration, and mixtures of compounds in the D- and L-configurations, unless otherwise specified. The naturally occurring D-configuration is preferred.

The compounds of the invention may be present in the form of their pharmaceutically acceptable salts, such as, but not limited to, an alkali metal salt such as sodium or potassium; an alkaline earth metal salt such as manganese, magnesium, or calcium; or an ammonium or tetraalkyl ammonium salt, i.e., $NX_4^+$ (wherein X is $C_{1-4}$). Pharmaceutically acceptable salts are salts that retain the desired biological activity of the parent compound and do not impart undesired toxicological effects.

The compounds of the invention may also be present in the form of prodrugs, typically comprising esters or amide moieties on the heterocyclic and furanosyl hydroxyls of the compound.

Another aspect of the present invention is a method of treating a mammal with vaginal dryness arising from, but not limited to, menopause, childbirth, breastfeeding, chemotherapy or radiotherapy, diabetes mellitus, Sjögren's syndrome, Ehlers-Danlos syndrome, systemic sclerosis and other systemic autoimmune diseases, hysterectomy, urogenital surgery, psychosomatic disorders, anxiety, psychosexual problems, and pharmacological drug-related side effects.

The present invention further provides pharmaceutical compositions comprising a $P2Y_6$ receptor agonist selected from the group consisting of general Formula I, i.e., uridine 5'-diphosphate [UDP] and its analogs, general Formula II, i.e., $P^1,P^4$-di(uridine-5') triphosphate [$U_2P_3$] and its analogs, general Formula III, i.e., cytidine 5'-diphosphate [CDP] and its analogs, and general Formula IV, i.e., adenosine 5'-diphosphate [ADP] and its analogs, together with a pharmaceutical carrier therefor.

The compounds disclosed herein may be administered to the mucosa of a patient by any suitable means, but are preferably administered by a solution, gel, suspension, cream, foam, pessary, or tablet containing the active compound. Alternatively, the active compounds may by administered by continuous release from a vaginal ring (P. Stumpf, *Obstet. Gynecol.* 75:9S (1990)) or an intrauterine device (K. Andersson, et al., *Obstet. Gynecol.* 79:963 (1992)).

The active compounds disclosed herein may be administered to the eyes of a patient by any suitable means, but are preferably administered by administering a liquid or gel suspension of the active compound in the form of drops, spray or gel. Alternatively, the active compounds may be applied to the eye via liposomes. Further, the active compounds may be infused onto the mucosal surface via a pump-catheter system. Another embodiment of the present invention involves the active compound contained within a continuous or selective-release device, for example, membranes such as, but not limited to, those employed in the Ocusert® System (Alza Corp., Palo Alto, Calif.). As an additional embodiment, the active compounds can be contained within, carried by, or attached to contact lenses which are placed on the eye. Another embodiment of the present invention involves the active compound contained within a swab or sponge which can be applied to the ocular surface. Another embodiment of the present invention involves the active compound contained within a liquid spray which can be applied to the ocular surface.

The topical solution, gel, jelly, ointment, cream, foam, pessary, or tablet contain the active compound in a physiologically compatible vehicle, as those skilled in the art of topical delivery system development can select using conventional criteria.

Solutions formulated for administration to the vagina are usually referred to as irrigations. These are sterile solutions, prepared in a manner typical of sterile injections that are intended for prepared as a single use sterile solution.

Gels or jellies may be produced using a suitable gelling agent including, but not limited to, gelatin, tragacanth, or a cellulose derivative and may include glycerol as a humectant, emollient, and preservative.

Ointments are semi-solid preparations that consist of the active ingredient incorporated into a fatty, waxy, or synthetic base.

Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Pessaries are solid unit-dose forms suitably shaped for insertion into the vagina and may either be composed of a base that melts at body temperature or which dissolves when in contact with mucous secretions. Examples of suitable bases include, but are not limited to, theobroma oil, synthetic fat bases (e.g. Witepsol), polyethylene glycols (macrogols), and glycerol suppository basis.

Tablets are composed of the active ingredient contained within a solid dosage form base which may include, but not be limited to, excipients such as lactose, microcrystalline cellulose, corn starch, magnesium stearate, silicon dioxide, and hydroxypropyl methylcellulose.

An alternative method of administering the compounds of the present invention is intraoperative instillation during surgical procedures involving mucosal surfaces of the eye, sinuses, mouth and female reproductive tract.

In addition to the topical method of administration described above, there are various methods of administering the compounds of the present invention systemically. One such means would involve an aerosol suspension of respirable particles comprised of the active compound, which the subject inhales. The active compound would be absorbed into the bloodstream via the lungs and contact the cervical and/or vaginal tissues in a pharmaceutically effective amount. The respirable particles may be liquid or solid, with a particle size sufficiently small to pass through the mouth and larynx upon inhalation; in general, particles ranging from about 1 to 10 microns, but more preferably 1–5 microns, in size are considered respirable.

Another means of systemically administering the active compounds to the mucosal tissues of the subject would involve administering a liquid/liquid suspension in the form of nasal drops of a liquid formulation, or a nasal spray of respirable particles which the subject inhales. Liquid pharmaceutical compositions of the active compound for producing a nasal spray or nasal drops may be prepared by combining the active compound with a suitable vehicle, such as sterile pyrogen free water or sterile saline by techniques known to those skilled in the art.

Other means of systemic administration of the active compound would involve oral administration, in which pharmaceutical compositions containing compounds of Formulas I, II, III, or IV are in the form of tablets, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide pharmaceutically elegant and palatable preparations. Tablets contain the active ingredient in admixture with nontoxic pharmaceutically acceptable excipients which are suitable for the manufacture of tablets. These excipients may be, for example, inert diluents, such as calcium carbonate, sodium carbonate, lactose, calcium phosphate, or sodium phosphate; granulating and disintegrating agents, for example, corn starch or alginic acid; binding agents, for example, starch, gelatin, or acacia; and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example, peanut oil, liquid paraffin, or olive oil.

Additional means of systemic administration of the active compound to the cervical and vaginal tissues of the subject would involve a suppository form of the active compound, such that a therapeutically effective amount of the compound reaches the mucosal tissues via systemic absorption and circulation.

For the above mentioned indications, the quantity of the active compound included in the pharmaceutical composition is an amount sufficient to achieve concentrations of the active compound on the mucosa of the subject of from about $10^{-7}$ to about $10^{-1}$ Moles/liter, and more preferably from about $10^{-6}$ to about $10^{-1}$ Moles/liter.

Depending upon the solubility of the particular formulation of active compound administered, the daily dose to promote tear secretion may be divided among one or several unit dose administrations. The total daily dose for UDP (for example) may range from 0.2 mg to 300 mg, depending upon the age and condition of the subject. A currently preferred unit dose for UDP is about 0.1 to 50 milligrams given at a regimen of 2 to 6 administrations per day.

Depending on the solubility of the particular formulation of active compound administered, the daily dose to promote mucous membrane mucin production and/or hydration may be divided among one or several unit dose administrations. The total daily dose for UDP (for example) may range from 1 to 1000 milligrams, depending upon the age and state of the subject, given at a regimen of up to four times per day or on an as needed basis to address acute exacerbations.

Some compounds of Formulas I, II, III, and IV can be made by methods which are well known to those skilled in the art and in accordance with known procedures (P. Zamecnik, et al., *Proc. Natl Acad. Sci. USA* 89:838–842 (1981); K. Ng et al., *Nucleic Acids Res.* 15:3572–3580 (1977); K. M. Jacobus, et al., U.S. Pat. No. 5,789,391 and W. Pendergast, et al., International Patent No. WO98/34942; Boucher, RC, Jr. et al., PCT/US98/17894) which are incorporated herein by reference; some are commercially available, for example, from Sigma Chemical Company, PO Box 14508, St. Louis, Mo. 63178. The synthetic methods of U.S. Pat. No. 5,789,391 and International Patent No. WO98/34942 are incorporated herein by reference.

EXAMPLE 1

UDP Stimulates Mucin Release From Human Mucosal Epithelial Cell Culture

The following is an example showing mucin release in response to UDP in an in vitro cell culture system containing mucosal epithelial and goblet cells. Mucins, a family of high-molecular-weight glycoproteins secreted by goblet and non-goblet epithelial cells of mucus membranes, are responsible for mucosal hydration. The objective of this study was to demonstrate the effect of UDP on mucin release in Normal Human Bronchial/Tracheal Epithelial cells (NHTBE).

NHTBE cells were obtained from a commercial source (Clonetics; CC-2540). The cells are donor specific (non-smoker) and shipped as cryopreserved primary cultures. Bronchial/Epithelial Growth Media (BEGM; Clonetics; CC-3170) was used for expansion. The BEGM media supplied was modified as follows: The level of EGF (Intergen; #4110–80) was increased to a final concentration of 25 ng/ml; the level of Bovine Pituitary Extract (BPE, Clonetics, CC 4009) was increased to 0.13 mg/ml; the level of retinoic acid (Sigma; R-2625) was increased to a final concentration of 5×10–8 M. The cells for the expansion phase were seeded at 500 cells/cm$^2$. Media was changed after 24 hours and every 48 hours thereafter until cells are 75% confluent (5–14 days). It was important not to exceed 75% confluency. Cells were dissociated with trypsin. Once collected, cells were stored in liquid nitrogen at passage-2 [Freezing solution: 80% media (BEGM), 10% FBS, 10% sterile DMSO].

NHTBE cells must undergo a program of differentiation in order to achieve a mucin-secreting phenotype. This was achieved by culturing cells on porous membrane cell culture inserts (Transwell™; 12 mm, 0.45 µm pore size, Corning-Costar #3460) ultimately under conditions of an air/liquid interface. The insert membrane was first coated with rat tail collagen (Collaborative Biomedical Products #40236) as follows: 235µl of coating solution(50 µg/ml of rat tail collagen dissolved in 0.02N acetic acid) was added to apical surface of insert. The insert was allowed to dry at room temperature for one hour in tissue culture hood and then washed once with 500 µl of PBS containing nystatin (20,000 units/liter sigma;N-1638) and gentamicin 100 µg/ml). Next, the 500 µPBS was aspirated and the inserts equilibrated with BEGM media in the apical and basal compartments; incubated for one hour. Frozen NHTBE cells were thawed rapidly and seeded on the collagen-coated inserts at 20,000 cells/cm$^2$. Media was changed after 24 hours and every 48 hours thereafter until the cells were 60–75% confluent (5–7 days in culture). At this point, the cultures were switched to air-liquid interface by removing the media bathing the apical aspect of the cells. The media bathing the basolateral aspect of the culture must be changed daily until the time of experiment. The composition of this ALI media was as follows: A 1:1 mixture of Bronchial epithelial cell growth medium: Dulbecco's Modified Eagles medium with high glucose (BEGM: DMEM-H), containing final concentration of 0.5 ng/ml hrEGF, 0.5 µ/ml hydrocortisone, 5 µg/ml insulin, 10 µg/ml transferrin, 0.5 µg/ml epinephrine, 6.5 ng/ml triiodothyronine, 50 µg/ml gentamicin, 50 ng/ml amphotericin-B (all supplied by Clonetics as SingleQuots), 8 mg/ml BPE, 5×10$^{-8}$ M all-trans retinoic acid (Sigma #R-2625), 1.5 µg/ml BSA (Intergen, #3310–80), and 20 U/ml nystatin (Sigma #N-1638). SingleQuots can be purchased separately from Clonetics (#CC-4175). As has been reported by Gray, et al., *Am J. Resp. Cell Molec. Biol.* 14(1):104–112 (1996), mucin phenotype was seen by 14 days in culture (7 days of air/liquid interface), and cilia were apparent by 21 days in culture (14 days of air/liquid interface).

Ascites fluid containing the anti-mucin antibody designated 17Q2 IgG was kindly provided by Professor Reen Wu; (Department of Internal Medicine, University of California at Davis). 17Q2 antibody was purified with a Protein G column (Pierce #44441). Alkaline phosphatase was conjugated to 17Q2 antibody using the EZ-Link Malemide Acitivated Alkaline Phosphatase kit (Pierce #31486).

UDP ($10^{-8} \sim 10^{-4}$) was added to the apical aspect of the differentiated cultures At the end of the incubation period (two hours) the stimulation media was removed and stored at –80° C. until analysis for mucin content. Mucin was quantitated by ELISA as described above.

UDP stimulated the release of mucin glycoproteins from differentiated cultures of human airway epithelium (FIG. 1) in a concentration-dependent manner. The $EC_{50}$ was calculated to be $5.55 \times 10^{-7}$ M.

EXAMPLE 2

Stimulation of Mucin Release from Mucosal Goblet Cells

The following is an example of a method for measuring the effects of UDP and analogs in vivo on mucin secretion from mucous membranes using impression cytology. Impression cytology is a technique used to stain and identify mucin-containing goblet cells (Rolando, M., et al., *Adv. Exp. Med. Bio.* 350:249 (1994)).

UDP or saline solution is applied to the mucosal surface and impression cytology is performed 5, 15, 30 and 60 minutes after application of solution. The specimens are stained with periodic acid and Schiff's reagent (AB-PAS), and the area of PAS staining is analyzed by compouter software (Winroof or BioQuant). A decrease in the area of AB-PAS staining compared to saline control indicates that UDP stimulates mucin secretion from goblet cells of mucus membranes.

The present invention is concerned primarily with the treatment of human subjects, but may also be employed for the treatment of other mammalian subjects, such as dogs and cats, for veterinary purposes.

The topical solution containing the active compound may also contain a physiologically compatible vehicle, as those skilled in the ophthalmic art can select using conventional criteria. The vehicles may be selected from the known ophthalmic vehicles which include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

An alternative method of administering the compounds of the present invention is intraoperative instillation during surgical procedures involving mucosal surfaces of the eye, sinuses, mouth and female reproductive tract.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method of stimulating mucosal hydration in a tissue other than the lung of a mammal in need thereof, comprising administering an effective hydration increasing amount of a compound of Formula I, II, III, or IV:

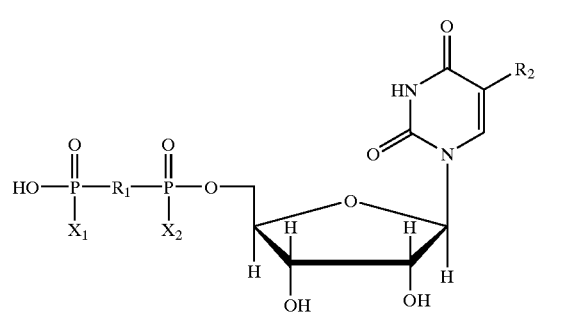

Formula I wherein:
$X_1$ and $X_2$ are each independently either O− or S−;
$R_1$ is O, imido, methylene or dihalomethylene;
$R_2$ is selected from the group consisting of: H, halo, alkyl, substituted alkyl, alkenyl and substituted alkenyl, alkynyl and substituted alkynyl, alkoxyl, nitro, and azido;

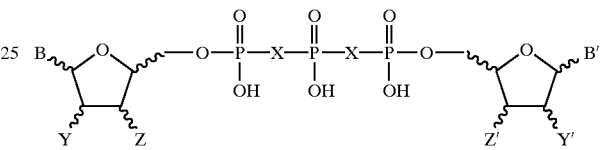

wherein:
X is oxygen, methylene, difluoromethylene, or imido;
B and B' are each independently a purine residue or a pyrimidine residue as depicted in Formula IIc or IId, linked through the 9- or 1-position, respectively;
Z=OH or $N_3$;
Z'=OH or $N_3$;
Y=H or OH;
Y'=H or OH;
provided that when Z is $N_3$, Y is H or when Z' is $N_3$, Y' is H;

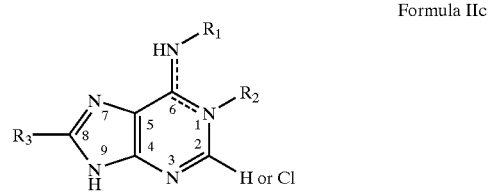

Formula IIc wherein
$R_1$ is hydrogen, $C_{1-8}$alkyl, $C_{3-6}$ cycloalkyl, phenyl, or phenyloxy; wherein at least one hydrogen of said $C_{1-8}$alkyl, phenyl, phenyloxy, is optionally substituted with a moiety selected from the group consisting of: halogen, hydroxy, $C_{1-4}$alkoxy, $C_{1-4}$alkyl, $C_{6-10}$aryl, carboxy, cyano, nitro, sulfonamido, sulfonate, phosphate, sulfonic acid, amino, $C_{1-4}$ alkylamino, and di-$C_{1-4}$ alkylamino wherein said alkyl groups are optionally linked to form a heterocycle, ω-A(alkyl) CONH(alkyl)-, and ω-A(alkyl)NHCO(alkyl)-, wherein A is amino, mercapto, hydroxy, or carboxyl;
$R_2$ is O or is absent; or
$R_1$ and $R_2$ taken together form a 5-membered fused imidazole ring optionally substituted on the 4- or 5- positions of the etheno moiety with $C_{1-4}$alkyl, phenyl or phenyloxy, wherein at least one hydrogen of said $C_{1-4}$alkyl, phenyl or phenyloxy, is optionally substituted with a moiety selected from the group consisting of: halogen, hydroxy, $C_{1-4}$alkoxy, $C_{1-4}$alkyl, $C_{6-10}$aryl, $C_{7-12}$arylalkyl, carboxy, cyano, nitro, sulfonamido, sulfonate, phosphate, sulfonic acid, amino, $C_{1-4}$ alkylamino, and di-$C_{1-4}$ alkylamino wherein said dialkyl groups are optionally linked to form a heterocycle; and $R_3$ is hydrogen, $NH_2$, $C_{1-8}$alkyl, $C_{3-6}$ cycloalkyl, phenyl, or phenyloxy, wherein at least one hydrogen of said $NH_2$, $C_{1-8}$alkyl, phenyl, or phenyloxy, is optionally substituted with a moiety selected from the group consisting of: halogen, hydroxy, $C_{1-4}$alkyl, $C_{6-10}$aryl, $C_{7-12}$arylalkyl, $C_{1-4}$alkoxy, $C_{7-12}$arylalkyloxy, $C_{1-4}$alkylthio, phenylthio, $C_{7-12}$arylalkylthio, carboxy, cyano, nito, sulfonamido, sulfonate, phosphate, sulfonic acid, amino, $C_{1-4}$alkylamino, phenylamino, $C_{7-12}$arylalkyamino, di-$C_{1-4}$ alkyl amino, wherein said di-$C_{1-4}$ alkyl groups are optionally linked to form a heterocycle, ω-A(alkyl)CONH(alkyl)B—, and ω-A(alkyl)NHCO(alkyl)B—, wherein A and B are independently amino, mercapto, hydroxy, or carboxyl;

Formula IId

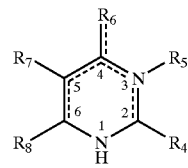

wherein:

$R_4$ is hydrogen, hydroxy, mercapto, amino, cyano, C7-12arylalkoxy, $C_{1-6}$ alkylthio, $C_{1-6}$ alkoxy, $C_{1-6}$ alkylamino, or di$C_{1-4}$alkylamino, wherein the alkyl groups are optionally linked to form a heterocycle;

$R_5$ is hydrogen, acetyl, benzoyl, $C_{1-6}$ alkyl, phenyloxy, $C_{1-5}$ alkanoyl, aroyl, or sulphonate;

$R_6$ is hydroxy, mercapto, $C_{1-4}$alkoxy, $C_{7-12}$arylalkoxy, $C_{1-6}$alkylthio, amino, S-phenyl, $C_{1-5}$ disubstituted amino, triazolyl, $C_{1-6}$alkylamino, or di-$C_{1-4}$alkylamino wherein said dialkyl groups are optionally linked to form a heterocycle or linked to $N^3$ to form a substituted ring; or $R_5$ and $R_6$ taken together form a 5-membered fused imidazole ring between positions 3 and 4 of the pyrimidine ring and form a 3, $N^4$-ethenocytosine derivative, wherein said etheno moiety is optionally substituted on the 4- or 5-positions with $C_{1-4}$ alkyl, phenyl or phenyloxy, wherein at least one hydrogen of said $C_{1-4}$alkyl, phenyl or phenyloxy is optionally substituted with a moiety selected from the group consisting of: halogen, hydroxy, $C_{1-4}$alkoxy, $C_{1-4}$alkyl, $C_{6-10}$aryl, $C_{7-12}$arylalkyl, carboxy, cyano, nitro, sulfonamido, sulfonate, phosphate, sulfonic acid, amino, $C_{1-4}$ alkylamino, and di- $C_{1-4}$ alkylamino, wherein said dialkyl groups are optionally linked to form a heterocycle;

$R_7$ is hydrogen, hydroxy, cyano, nitro, or $C_{2-8}$alkenyl; wherein said alkenyl moiety is optionally linked through an oxygen to form a ring, wherein at least one hydrogen of said alkenyl moiety on the carbon adjacent to said oxygen is optionally substituted with $C_{1-6}$alkyl, phenyl, substituted $C_{2-8}$galkynyl, halogen, substituted $C_{1-4}$alkyl, $CF_3$, $C_{2-3}$ alkenyl, $C_{2-3}$ alkenyl, allylamino bromovinyl, ethyl propenoate, or propenoic acid; or $R_6$ and $R_7$ together form a 5- or 6-membered saturated or unsaturated ring bonded through N or O at $R_6$, such ring optionally contains substituents that themselves contain functionalities; provided that when $R_8$ is amino or substituted amino, $R_7$ is hydrogen; and $R_8$ is hydrogen, amino or di-$C_{1-4}$alkylamino, $C_{1-4}$alkoxy, $C_{7-12}$arylalkoxy, $C_{1-4}$alkylthio, $C_{7-12}$arylalkylthio, carboxarnidomethyl, carboxymethyl, methoxy, methylthio, phenoxy, or phenylthio;

Formula III

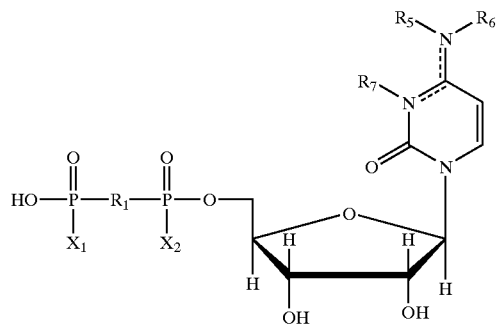

wherein:

$R_1$, $X_1$ and $X_2$ are defined as in Formula I;

$R_5$ and $R_6$ are H while $R_7$ is nothing and there is a double bond between N-3 and C-4, or $R_5$, $R_6$ and $R_7$ taken together are —CH=CH—, forming a ring from N-3 to N-4 with a double bond between N-4 and C-4 optionally substituted at the 4- or 5-position of the etheno ring;

Formula IV

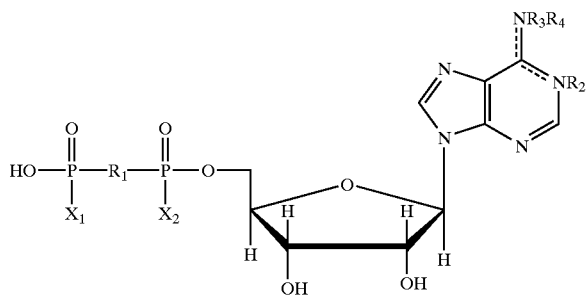

wherein:

$R_1$, $X_1$ and $X_2$ are defined as in Formula I;

$R_3$ and $R_4$ are H while $R_2$ is nothing and there is a double bond between N-1 and C-6, or $R_3$ and $R_4$ are H while $R_2$ is O and there is a double bond between N-1 and C-6, or $R_3$, $R_4$, and $R_2$ taken together are —CH=CH—, forming a ring from N-6 to N-1 with a double bond between N-6 and C-6.

2. A method of stimulating mucosal hydration in a tissue selected from the group consisting of eye, vagina, sinonasal cavities and mouth of a mammal in need thereof, comprising administering an effective hydration increasing amount of a compound of Formula I, II, III, or IV:

Formula I

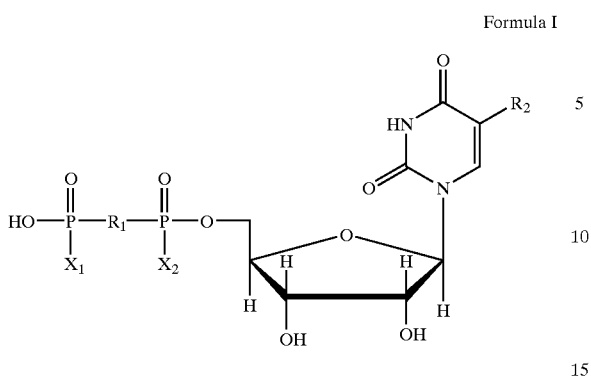

wherein:

$X_1$ and $X_2$ are each independently either O– or S–;

$R_1$ is O, imido, methylene or dihalomethylene;

$R_2$ is selected from the group consisting of: H, halo, alkyl, substituted alkyl, alkenyl and substituted alkenyl, alkynyl and substituted alkynyl, alkoxyl, nitro, and azido;

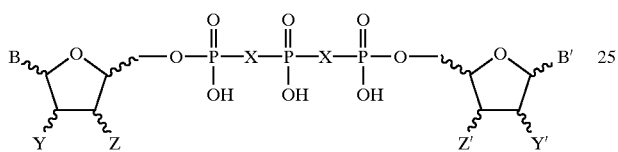

wherein:

X is oxygen, methylene, difluoromethylene, or imido;

B and B' are each independently a purine residue or a pyrimidine residue as depicted in Formula IIc or IId, linked through the 9- or 1-position, respectively;

Z=OH or $N_3$;

Z'=OH or $N_3$;

Y=H or OH;

Y'=H or OH;

provided that when Z is $N_3$, Y is H or when Z' is $N_3$, Y' is H;

Formula IIc

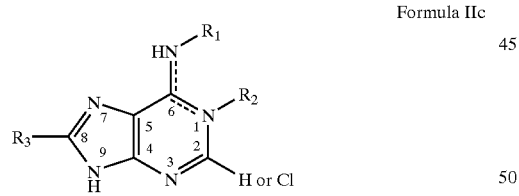

wherein $R_1$ is hydrogen, $C_{1-8}$alkyl, $C_{3-6}$ cycloalkyl, phenyl, or phenyloxy; wherein at least one hydrogen of said $C_{1-8}$alkyl, phenyl, phenyloxy, is optionally substituted with a moiety selected from the group consisting of: halogen, hydroxy, $C_{1-4}$alkoxy, $C_{1-4}$alkyl, $C_{6-10}$aryl, carboxy, cyano, nitro, sulfonamido, sulfonate, phosphate, sulfonic acid, amino, $C_{1-4}$ alkylamino, and di-$C_{1-4}$ alkylamino wherein said alkyl groups are optionally linked to form a heterocycle, ω-A(alkyl)CONH(alkyl)-, and ω-A(alkyl)NHCO(alkyl)-, wherein A is amino, mercapto, hydroxy, or carboxyl;

$R_2$ is O or is absent; or $R_1$ and $R_2$ taken together form a 5-membered fused imidazole ring optionally substituted on the 4- or 5- positions of the etheno moiety with $C_{1-4}$alkyl, phenyl or phenyloxy, wherein at least one hydrogen of said $C_{1-4}$alkyl, phenyl or phenyloxy, is optionally substituted with a moiety selected from the group consisting of: halogen, hydroxy, $C_{1-4}$alkoxy, $C_{1-4}$alkyl, $C_{6-10}$aryl, $C_{7-12}$arylalkyl, carboxy, cyano, nitro, sulfonamido, sulfonate, phosphate, sulfonic acid, amino, $C_{1-4}$ alkylamino, and di-$C_{1-4}$ alkylamino wherein said dialkyl groups are optionally linked to form a heterocycle; and $R_3$ is hydrogen, $NH_2$, $C_{1-8}$alkyl, $C_{3-6}$ cycloalkyl, phenyl, or phenyloxy, wherein at least one hydrogen of said $NH_2$, $C_{1-8}$ alkyl, phenyl, or phenyloxy, is optionally substituted with a moiety selected from the group consisting of: halogen, hydroxy, $C_{1-4}$alkyl, $C_{6-10}$aryl, $C_{7-12}$arylalkyl, $C_{1-4}$alkoxy, $C_{7-12}$arylalkyloxy, $C_4$alkylthio, phenylthio, $C_{7-12}$arylalkylthio, carboxy, cyano, nitro, sulfonamido, sulfonate, phosphate, sulfonic acid, amino, $C_{1-4}$ alkylamino, phenylamino, $C_{7-12}$arylalkyamino, and di-$C_{1-4}$ alkyl amino, wherein said di-$C_{1-4}$ alkyl groups are optionally linked to form a heterocycle, ω-A(alkyl)CONH(alkyl)B—, and co-A(alkyl)NHCO(alkyl)B—, wherein A and B are independently amino, mercapto, hydroxy, or carboxyl;

Formula IId

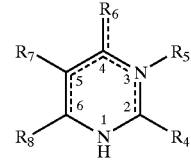

wherein:

$R_4$ is hydrogen, hydroxy, mercapto, amino, cyano, $C_{7-12}$arylalkoxy, $C_6$ alkylthio, $C_{1-6}$ alkoxy, $C_{1-6}$ alkylamnino, or di$C_{1-4}$alkylamino, wherein the alkyl groups are optionally linked to form a heterocycle;

$R_5$ is hydrogen, acetyl, benzoyl, $C_{1-6}$ alkyl, phenyloxy, $C_{1-5}$ alkanoyl, aroyl, or sulphonate;

$R_6$ is hydroxy, mercapto, $C_{1-4}$alkoxy, $C_{7-12}$arylalkoxy, $C_{1-6}$alkylthio, amino, S-phenyl, $C_5$ disubstituted amino, triazolyl, $C_{1-6}$alkylamino, or di-$C_{1-4}$alkylamino wherein said dialkyl groups are optionally linked to form a heterocycle or linked to $N^3$ to form a substituted ring; or $R_5$ and $R_6$ taken together form a 5-membered fused imidazole ring between positions 3 and 4 of the pyrimidine ring and form a 3, $N^4$-ethenocytosine derivative, wherein said etheno moiety is optionally substituted on the 4- or 5 -positions with $C_{1-4}$alkyl, phenyl or phenyloxy, wherein at least one hydrogen of said $C_{1-4}$alkyl, phenyl or phenyloxy is optionally substituted with a moiety selected from the group consisting of: halogen, hydroxy, $C_{1-4}$alkoxy, $C_{1-4}$alkyl, $C_{6-10}$aryl, $C_{7-12}$arylalkyl, carboxy, cyano, nitro, sulfonamido, sulfonate, phosphate, sulfonic acid, amino, $C_{1-4}$ alkylamino, and di-$C_{1-4}$alkylamino, wherein said dialkyl groups are optionally linked to form a heterocycle;

$R_7$ is hydrogen, hydroxy, cyano, nitro, or $C_{2-8}$alkenyl; wherein said alkenyl moiety is optionally linked through an oxygen to form a ring, wherein at least one hydrogen of said alkenyl moiety on the carbon adjacent to said oxygen is optionally substituted with $C_{1-6}$alkyl, phenyl, substituted $C_{2-8}$alkynyl, halogen, substituted $C_{1-4}$alkyl, $CF_3$, $C_{2-3}$ alkenyl, $C_{2-3}$ alkynyl, allylamino, bromovinyl, ethyl propenoate, or propenoic acid; or $R_6$ and $R_7$ together form a 5- or 6-membered saturated or unsaturated ring bonded through N or O at $R_6$, such ring optionally contains substituents that themselves contain functionalities; provided that when $R_8$ is amino or substituted amino, $R_7$ is hydrogen; and $R_8$ is hydrogen, amino or di-$C_{1-4}$alkylamino, $C_{1-4}$alkoxy, $C_{7-12}$arylalkoxy, $C_{1-4}$alkylthio, $C_{7-12}$arylalkylthio, carboxamidomethyl, carboxymethyl, methoxy, methylthio, phenoxy, or phenylthio;

Formula III

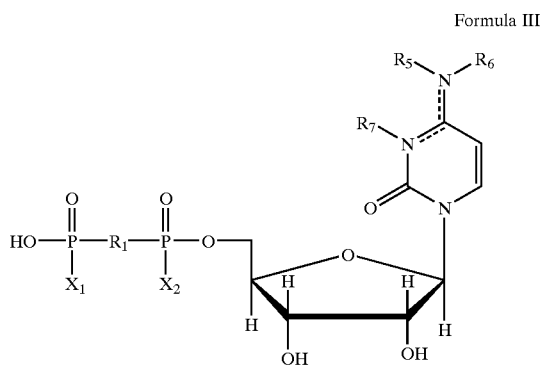

wherein $R_1$, $X_1$ and $X_2$ are defined as in Formula I;

$R_5$ and $R_6$ are H while $R_7$ is nothing and there is a double bond between N-3 and C-4, or $R_5$, $R_6$ and $R_7$ taken together are —CH=CH—, forming a ring from N-3 to N-4 with a double bond between N-4 and C-4 optionally substituted at the 4- or 5-position of the etheno ring;

Formula IV

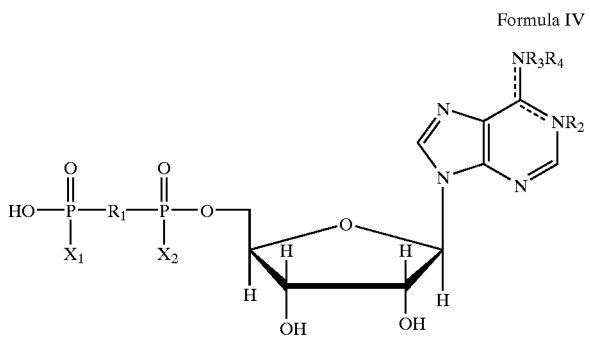

wherein:

$R_1$, $X_1$ and $X_2$ are defined as in Formula I;

$R_3$ and $R_4$ are H while $R_2$ is nothing and there is a double bond between N-1 and C-6, or $R_3$ and $R_4$ are H while $R_2$ is O and there is a double bond between N-1 and C-6, or $R_3$, $R_4$, and $R_2$ taken together are —CH=CH—, forming a ring from N-6 to N-1 with a double bond between N-6 and C-6.

3. The method of claim 2, wherein the effective hydration increasing amount of compound of Formula I, II, III, or IV is administered to the eyes to treat dry eye disease.

4. The method of claim 2, wherein the effective hydration increasing amount of compound of Formula I, II, III, or IV is administered to the eyes to treat corneal injury.

5. The method of claim 2, wherein the effective hydration increasing amount of compound of Formula I, II, III, or IV is administered to the sinuses to treat rhinosinusitis.

6. The method of claim 2, wherein the effective hydration increasing amount of compound of Formula I, II, III, or IV is administered to the mouth to treat dry mouth disease.

7. The method of claim 2, wherein the effective hydration increasing amount of compound of Formula I, II, III, or IV is administered to the vagina to treat vaginal dryness.

8. The method of claim 3, wherein said compound is UDP.

9. A method for detecting a lung disease comprising the steps of:

administering to at least one lung of a subject an expectoration increasing amount of a compound of Formula I, II, III, or IV as depicted in claim 1 to facilitate the expectoration of sputum;

obtaining a deep lung mucus from a sputum sample;

subjecting said deep lung mucus to an analysis; and detecting cellular abnormalities in the lung ephithelium.

10. The method of claim 9, wherein the lung disease is lung cancer or tuberculosis.

11. The method of claim 9, wherein the analysis comprises cytological analysis, immunocytochemical analysis, bacterial analysis and DNA analysis.

12. The method of claim 9, wherein said compound is UDP.

* * * * *